US00PP08302P

United States Patent [19]

Vletter

[11] Patent Number: Plant 8,302

[45] Date of Patent: Jul. 13, 1993

[54] LILY PLANT NAMED VIVALDI

[75] Inventor: Floris Vletter, Rijnsburg, Netherlands

[73] Assignee: Gebr. Vletter & J. A. Den Haan, Rijnsburg, Netherlands

[21] Appl. No.: 796,529

[22] Filed: Nov. 21, 1991

[51] Int. Cl.[5] ..... A01H 5/00

[52] U.S. Cl. ..... Plt./87.4

[58] Field of Search ..... Plt./87.4

*Primary Examiner*—James R. Feyrer

*Attorney, Agent, or Firm*—Foley & Lardner

[57] ABSTRACT

A new and distinct lily plant named Vivaldi, characterized by its soft pink flower color, long flower stems, relatively flat flower form, red-purple markings, and its vigorous growth habit.

1 Drawing Sheet

The present invention comprises a new and distinct cultivar of lily, botanically known as Lilium, commercially known as Lilium asiatic hybrid, and hereinafter referred to by the cultivar name Vivaldi. The parents were asiatic varieties belonging to division I described in "Classification of Lily Cultivars into Divisions" published by Victoria Mathews, The Royal Botanic Gardens, Kew (1989).

The new cultivar is a product of a planned breeding program which had the objectives of creating new lily cultivars having a new and distinct pink color, a flatter flower, and other desired characteristics for cut flower production.

The new cultivar was originated from a hybridization made by the inventor in a controlled breeding program in Rijnsburg, The Netherlands in 1984. The female parent was an unnamed seedling. The male parent was the cultivar Sanciro.

The new cultivar was discovered and selected as one flowering plant within the progeny of the stated cross by the inventor in June 1984 in a controlled environment in Rijnsburg, The Netherlands.

The first act of asexual reproduction of the new cultivar was accomplished by the inventor when scales were taken from the initial selection in 1987 in a controlled environment in Rijnsburg, The Netherlands.

Horticultural examination of selected units has demonstrated that the combination of characteristics as herein disclosed for Vivaldi are firmly fixed and are retained through successive generations of asexual reproduction.

The new cultivar has not been observed under all possible environmental conditions. The phenotype may vary significantly with variations in environment such as temperature, light intensity, and day length, without, however, any variation in genotype. The following observations, measurements and comparisons describe plants grown in Wageningen and Rijnsburg, The Netherlands under greenhouse conditions which approximate those generally used in commercial practice.

The following traits have been repeatedly observed and are determined to be basic characteristics of the new cultivar which in combination distinguish this lily as a new and distinct cultivar.

1. Unique soft pink flower color;
2. Long flower stems;
3. Relatively flat flower form;
4. Vigorous growth habit.

Of the many commercial cultivars known to the present inventor, the most similar in comparison to the new cultivar is Monte Rosa, disclosed in my U.S. Plant Pat. No. 7,091. In comparison to Monte Rosa, Vivaldi has a lighter pink flower color, flatter tepals, more colored spots on inner tepals, and a more plain flower form with less bending or downward reflexing of the tips of the tepals. When flowering is forced under natural light, Vivaldi produces an inflorescence approximately 98 days earlier than Stargazer, under the same growing conditions. Vivaldi is fertile.

The accompanying photographic drawing shows typical flower characteristics of the new cultivar, with colors being as true as possible with illustrations of this type. The photograph comprises a top perspective view showing several flowers open and buds at various stages.

In the following description, color references are made to The Royal Horticultural Society (R.H.S.) Color Chart. The color values were determined at Wageningen in 1989–1990 and Rijnsburg in July 1991.

Origin: Seedling from Breeding Program.

Parentage:

*Seed parent.*—Unnamed seedling.

*Pollen parent.*—Sanciro.

Classification:

*Botanical.*—Lilium.

*Commercial.*—Asiatic hybrid.

THE PLANT

Form: A single stem carrying numerous pedicels alternately arranged.

Height: Tall; 130 cm at time of opening of anthers of first flower.

Growth habit: Vigorous.

Stem: Green 145B; grooved in transverse section; internodal length 2 cm and uniform; no anthocyanin pigmentation.

Foliage:

*Quantity.*—105–125 leaves depending on growing conditions.

*Size of leaf.*—Mature leaves are short to medium in length (15 cm), and medium to narrow in width (1.5 cm).

*Shape of leaves.*—Elliptical.

*Texture.*—Smooth with strong glossiness on upper side.

*Color.*—Medium green 137A.

Bulbs:

*Size.*—Outlet 6–22 cm.

*Color.*—White.

Roots: Both stem and contractile present.

THE BUD

Form: Tapering (like a lancet).

Size: 7 cm prior to opening.

Opening: Unfolds normally.

Color: 65A.

Tepals: Folded, three visible.

THE FLOWER

Blooming habit: Raceme.

Size: 14 cm in total diameter, depending on growing conditions.

Borne: Upright.

Shape: Generally in form of hexagonal star; bowl-shaped in cross-section, with tips bent downwardly.

Tepalage:

*Number of tepals.*—Six.

*Arrangement.*—Three inner and three outer.

*Color.*—Upper surface: Pink 62B-C; somewhat variegated, with sides of tepals being slightly darker but non-uniformly. Lower surface: Light pink 62D, sides of tepals near 62C.

*Spotting or marking.*—Dark red-purple spots approximately 2 mm in diameter; spots located on basal portion of tepals on each side of nectaries.

Nectaries and papillae: Present.

Pedicel:

*Length.*—12 cm.

*Color.*—Medium green.

*Form.*—Slightly curved; smooth.

Texture: Ribbed and papillose.

Disease resistance: No disease problems noted to date.

Fragrance: Absent.

Lasting quality: Excellent.

REPRODUCTIVE ORGANS

Stamens, anthers:

*Arrangement.*—Anthers form a generally circular pattern.

*Length.*—Short to very short, 3.5 cm.

*Number.*—Six.

*Filaments.*—White to green.

Pollen color: Deep yellow.

Anther color: Orange brown.

Pistils: One with green style; total length pistil 5.5 cm.

Stigma: Purple red stigma.

Ovaries: Triangular in shape; other characteristics typical of asiatic lily varieties.

I claim:

1. A new and distinct lily plant named Vivaldi, as illustrated and described.

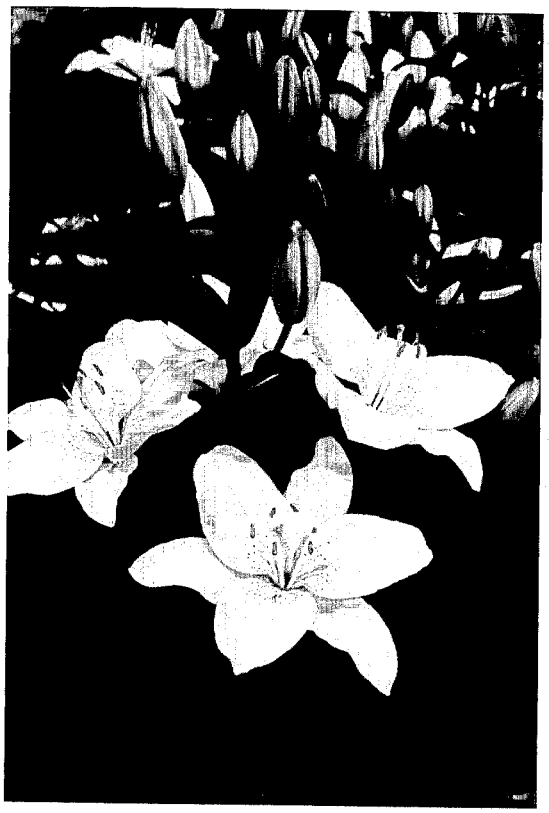

* * * * *